United States Patent [19]

Young

[11] 3,945,798

[45] Mar. 23, 1976

[54] FORMALDEHYDE TEST ELEMENT AND METHOD OF USE

[75] Inventor: David J. Young, Chorleywood, England

[73] Assignee: Eastman Kodak Company, Rochester, N.Y.

[22] Filed: May 20, 1974

[21] Appl. No.: 471,637

[30] Foreign Application Priority Data

May 24, 1973 United Kingdom............... 24799/73

[52] U.S. Cl. ........................... 23/230 R; 23/253 TP
[51] Int. Cl.² ......................................... G01N 31/22
[58] Field of Search ..................... 23/253 TP, 230 R

[56] References Cited
UNITED STATES PATENTS

| | | |
|---|---|---|
| 3,092,463 | 6/1963 | Adams, Jr. et al............... 23/253 TP |
| 3,099,605 | 7/1963 | Free .................................. 23/253 TP |
| 3,232,710 | 2/1966 | Rieckmann et al.............. 23/253 TP |
| 3,252,762 | 5/1966 | Adams, Jr. et al............... 23/253 TP |
| 3,290,228 | 12/1966 | Gretton et al................ 23/253 TP X |
| 3,443,903 | 5/1969 | Haack et al...................... 23/253 TP |
| 3,447,905 | 6/1969 | Shand ......................... 23/253 TP X |
| 3,502,437 | 3/1970 | Mass ................................ 23/253 TP |
| 3,544,275 | 12/1970 | Habermas et al............. 23/253 R X |
| 3,635,677 | 1/1972 | Drake, Jr. et al........... 23/253 TP X |
| 3,642,450 | 2/1972 | Eriksson.......................... 23/253 TP |
| 3,645,696 | 2/1972 | Iannacone et al............... 23/253 TP |
| 3,837,809 | 9/1974 | Chapman......................... 23/253 TP |
| 3,843,325 | 10/1974 | Schmitt et al..................... 23/230 R |

OTHER PUBLICATIONS

Blaedel et al., "Colorimetric Determination of Formaldehyde in the Presence of Other Aldehydes"; Anal. Chem., Vol. 13, 1941, pp. 449–450.
Kramm et al. "Schiff Reagent"; Anal. Chem., Vol. 27, 1955, pp. 1076–1079.
Nauman et al. "A Spectrophotometric Study of the Schiff Reaction as Applied to the Quantitative Determination of $SO_2$; Anal. Chem., Vol. 32, 1960, pp. 1307–1311; Group 171.

*Primary Examiner*—Morris O. Wolk
*Assistant Examiner*—Arnold Turk
*Attorney, Agent, or Firm*—G. W. Neuner

[57] ABSTRACT

A test element is provided which can detect and measure extremely low concentrations of formaldehyde in the environment. The test strip comprises a support having thereon a formaldehyde-sensitive layer comprising an inert formaldehyde-permeable binder which stabilizes sulphite ions against aerial oxidation having dispersed therein pararosaniline or an acid derivative thereof and sulphite ions. The test element requires no processing and can be fixed to obtain a permanent record.

9 Claims, No Drawings

FORMALDEHYDE TEST ELEMENT AND METHOD OF USE

This invention relates to a test element for detecting very low levels of formaldehyde.

Formaldehyde is widely distributed in both the industrial and domestic environment and can have harmful effects on, for example, both people and photographic products. For example, formaldehyde can often be released from paints, glues, insecticides, engine exhaust gases and wood products such as plywood and particle board. There is, therefore, a considerable need for a simple formaldehyde monitor.

There is a very extensive literature on the detection and estimation of formaldehyde. This is well summarized to 1964 by J. F. Walker in "Formaldehyde" (Reinhold, N.Y.), and more recently, with a photographic emphasis, by Dr. D. A. Thomas in an M.Sc. thesis (University of London, July, 1971). All the work described however involves bulk liquids for volumetric, colorimetric, gravimetric, or polarographic analysis.

One such method for detecting formaldehyde is disclosed in a paper entitled "17 Quantitative Determination of Formaldehyde in the Parts Per Hundred Million Concentration Level" by Lyles, Dowling, and Blanchard. (J. Air Pollution Control Association 15, 106–8, (1965)). These authors describe a colorimetric method using pararosaniline hydrochloride and a dichlorosulphitomercurate (II) complex for atmospheric testing. It is necessary to make up the mercury complex fresh each day.

It is therefore an object of the present invention to provide a novel method for using the change of color of a reagent containing layer to determine the concentration of formaldehyde.

It is an object of the present invention to provide a simple method and a test element for determining the concentration of formaldehyde which does not require further processing.

It is also an object of the present invention to provide a test element which is sensitive to very low levels of formaldehyde.

It is another object of the present invention to provide a test element which can be stored safely until used and then fixed for a permanent record.

These and further objects are accomplished by the present invention which provides a test element for detecting the presence of formaldehyde. The test element comprises a support having coated thereon a layer which is sensitive to the presence of formaldehyde. The formaldehyde sensitive layer comprises an inert (to formaldehyde) formaldehyde-permeable binder which stabilizes sulphite ion against aerial oxidation having sulphite ions and pararosaniline or an acid salt thereof dispersed therein. Preferably, the binder is gelatin. Upon exposure to formaldehyde, a visible, spectrophotometrically quantizable dye is formed. The concentration of dye is directly proportional to the concentration of formaldehyde in the environment and the time of exposure.

According to the invention, the support can be any suitable material known for such use in photography or other similar arts. Examples of such supports include paper, resin-coated paper and polymeric films such as cellulose acetate and poly(ethylene terephthalate), glass, wood and metal. It is preferred that the support be transparent to light so that the transmission density of the colored exposed formaldehyde sensitive layer may be ascertained. This is not necessary, however, since the reflection density of the exposed layer may be ascertained when translucent or opaque supports are used by conventional reflective or transmissive techniques. Poly(ethylene terephthalate) is an especially preferred support because it is impermeable to formaldehyde and demonstrates the preferred transparency desirable for transmissive analysis of dye density.

The sulphite ions can be provided by using any suitable compound which is well known to those of average skill in the art. Thus, any sulphite compound which will release sulphite ion on contact with formaldehyde to produce a dye with the pararosaniline may be used. A preferred method of providing the sulphite ions is by using an alkali metal sulphite such as sodium, potassium or lithium sulphite.

Pararosaniline or an acid salt of pararosaniline can be used in the formaldehyde sensitive composition. A particularly useful acid salt is pararosaniline hydrochloride.

The binder should comprise a material or mixture of materials which in addition to serving the function of providing a matrix for the dispersed reagents and being readily and uniformly permeable to formaldehyde, also serves to stabilize sulphite ions against aerial oxidation. A particularly preferred binder for this purpose is gelatin, although any other material or mixture of materials possessing the foregoing characteristics may be used for this purpose.

In addition to the binder, sulphite ions and pararosaniline, the composition may contain a hygroscopic agent to increase the humidity in the formaldehyde sensitive layer of the test element. Any conventional hygroscopic agent may be used. A particularly useful hygroscopic agent is, for example, calcium chloride. The composition may also contain a mordant for the dye which is formed upon exposure to formaldehyde if this is desirable.

The formaldehyde-sensitive layer may be coated on the support by techniques well known in the photographic art and the coating composition may contain any other known additive, for example, surfactants, lubricants, plasticizers and the like.

Useful results may be obtained with a formaldehyde-sensitive layer containing various quantities of the above-named constituents. Typically, useful results can be obtained with a layer containing from about 0.2 to 2.0 g. of pararosaniline hydrochloride and up to 7.0 g. sulphite ions per 100 g. of binder. Calcium chloride, if used, may typically be present in an amount of up to 25 g of $CaCl_2 \cdot 2H_2O$ per 100 g. of gelatin.

The formaldehyde-sensitive layer may have a thickness in the range 5–50 $\mu$, the thinner layers providing, in photographic terms, a higher speed and lower maximum density and the thicker layers a lower speed and higher maximum density. The layers may typically contain the following components in amounts expressed as mg per square decimeter:

| Component | Amount $mg/dm^2$ |
|---|---|
| Gelatin | 100 – 5000 |
| Pararosaniline · HCl | 0.2 – 20 |
| Sodium sulphite · $7H_2O$ | 1.0 – 100 |

While the mechanism of the pararosaniline reaction used herein is not entirely known, it appears that the pararosaniline is decolorized by the acid conditions, and the sulphite ion and formaldehyde react to give sulphurous acid which condenses with the anilinium ion to give a dye.

In use, the present material is placed in the environment to be tested for a period of a few minutes up to a few days. In the presence of formaldehyde the dye starts to form immediately. It is a relatively simple matter to construct calibration curves whereby the density of the dye can be shown to be dependent on the concentration of formaldehyde and/or time of exposure, humidity being kept constant.

The density of the dye may be determined using a densitometer or, less accurately, by comparison with standard densities.

The material of the present invention can be made very sensitive and can detect concentrations of formaldehyde down to even below 1 part per million. Because of this and the constant presence of formaldehyde in the atmosphere, precautions will usually have to be taken to prevent the premature formation of the dye.

In one embodiment of the present invention, therefore, there is provided a material having a formaldehyde-impermeable base carrying the formaldehyde-sensitive layer and temporarily adhered to the surface of the layer, a formaldehyde-impermeable cover which may be removed prior to use. Formaldehyde-impervious materials include poly(vinyl chloride) (PVC) and poly(ethylene terephthalate).

After the dye has been formed further dye formation can be prevented by fixing. The fixing process can be accomplished by oxidizing any excess sulphite ions such as by using an acid dichromate bath, or alternatively by attaching a formaldehyde-impermeable material to the surface of the test element such as by attaching a self-adhesive polyvinyl chloride film.

In the event that the present material is intended for use by those without access to a densitometer, standard comparison dyes may be incorporated into the material itself or its packing to facilitate reading and quantifying the result.

The invention is further illustrated by the following examples:

EXAMPLE 1

3.0 g. of gelatin is dissolved in 10 ml of water at about 60°C and to this is added 75 mg of anhydrous sodium sulphite, 0.5 g of calcium chloride dihydrate, 2.0 ml. of a 1% aqueous mucochloric acid solution and 7.5 ml. of an acid solution of 0.16% pararosaniline hydrochloride prepared by dissolving 0.16 g. of pararosaniline hydrochloride in 24 ml. of concentrated hydrochloric acid and diluting to 100 ml. with water.

The solution is coated in two passes onto a 10 × 80 cm loop of subbed polyethylene terephthalate film base to give a glass clear dried layer about 50 $\mu$ thick.

Samples of a film prepared by the method above develop a magenta color when exposed to an atmosphere containing formaldehyde. A control area on the film may be obtained by covering the gelatin layer with some self-adhesive PVC tape. This area will remain uncolored after exposure to formaldehyde.

This film is so sensitive that if left exposed to room air for a few days the background becomes distinctly magenta. Two methods used to "fix" the film in order to provide a permanent record after it has been used for a formaldehyde determination are illustrated by Examples 2 and 3.

EXAMPLE 2

An exposed sample of a film prepared as in Example 1 with a control area is bathed for 30 seconds in an aqueous solution of 0.2% sodium dichromate and 0.03% sulphuric acid. It is then quickly washed and dried. A slight loss of magenta density (from 2.1 to 1.7) is noticed. This film is then placed in a formaldehyde atmosphere (1000 ppm, 58% R.H.) for 24 hours. The clear control area is unaffected.

In similar conditions, an untreated sample of film produces the maximum magenta density (of 2.1) in just 2 hours.

EXAMPLE 3

The film may be "mechanically" fixed by pressing a strip of self-adhesive PVC tape onto the gelatin surface. Two pieces of film, coated as in Example 1, are placed in a high concentration of formaldehyde (100 ppm) and removed before the maximum density is reached. One is fixed by applying a strip of self-adhesive PVC tape to its gelatin surface. The other is used as a contro. Both pieces of film are kept in a normal laboratory environment. The control reaches its maximum density in a few days, however, after months in the normal laboratory atmosphere the fixed film shows negligible increase of density.

Example 4

Small samples of a film prepared as in Example 1 are stood in a range of formaldehyde atmospheres of constant relative humidity and known formaldehyde concentration. A Blank control area is produced on the film by sticking a small piece of transparent adhesive P.V.C. tape to the gelatin surface. After calibrating the film prepared above, some of the film was stored at room temperature with a PVC tape protecting layer for 7 weeks. After 7 weeks, the film was recalibrated; no loss of sensitivity or rise in background is observed.

EXAMPLE 5

Samples of a formaldehyde sensitive film as prepared in Example 1 are stood in closed vessels containing the following compounds for 24 hours:

| | |
|---|---|
| Acetaldehyde | Chloral hydrate |
| Propionaldehyde | Acrolein |
| Butyraldehyde | Formic acid |
| Benzaldehyde | Mucochloric acid |
| Crotonaldehyde | Hexamethylene tetramine |
| Fural | Sulphur dioxide |

The only compound that shows a similar effect to that found with formaldehyde is propionaldehyde. The homologues, acetaldehyde and butyraldehyde show no discernable effect.

The invention has been described in detail with particular reference to certain preferred embodiments thereof, but it is understood that variations and modifications can be effected within the spirit and scope of the invention.

I claim:

1. An element for determining the amount of formaldehyde present in a gaseous environment comprising a support having thereon a formaldehyde-sensitive layer comprising gelatin, pararosaniline or an acid derivative thereof, a sulphite ion and a hygroscopic agent.

2. The element of claim 1 wherein the hygroscopic agent is calcium chloride.

3. The element of claim 1 wherein the support is a formaldehyde-impermeable transparent polymeric film selected from the group consisting of poly(ethylene terephthalate) and poly(vinyl) chloride), and the formaldehyde-sensitive layer comprises gelatin, pararosaniline hydrochloride, an alkali metal sulphite, and calcium chloride.

4. An element for determining the amount of formaldehyde present in a gaseous environment comprising (1) a formaldehyde-impermeable support having thereon a formaldehyde-sensitive layer comprising gelatin, pararosaniline hydrochloride, an alkali metal sulphite, and a hygroscopic agent; and (2) a strippable, formaldehyde-impermeable layer contiguous with the gelatin layer which can be removed from the gelatin layer prior to exposure.

5. The element of claim 4 wherein the formaldehyde-impermeable support and strippable layer are a polymeric film selected from the group consisting of poly(ethylene terephthalate) and poly(vinyl chloride).

6. A method for determining the quantity of formaldehyde present in a gaseous environment comprising:

exposing a test strip to a formaldehyde-containing gaseous environment, said test strip comprising a support having thereon a formaldehyde-sensitive layer comprising gelatin, pararosaniline or an acid derivative thereof, and sulphite ion, the exposed test strip producing a dye in the formaldehyde-sensitive layer in proportion to the concentration of formaldehyde in the environment and the exposure time; and determining the quantity of formaldehyde present from the density of the dye produced.

7. The method of claim 6 including the additional step of fixing the exposed test strip to obtain a permanent record.

8. The method of claim 7 wherein the fixing step comprises chemically oxidizing the excess sulphite ions.

9. The method of claim 7 wherein the fixing step comprises placing a formaldehyde-impermeable layer over the formaldehyde-sensitive layer to prevent further reaction.

* * * * *